United States Patent
Ruan et al.

(10) Patent No.: US 10,066,052 B2
(45) Date of Patent: Sep. 4, 2018

(54) DOCETAXEL NANO-POLYMER MICELLE LYOPHILIZED PREPARATION AND PREPARATION METHOD THEREOF

(71) Applicant: SUZHOU HIGH-TECH BIOSCIENSE CO., LTD, Taicang, Suzhou (CN)

(72) Inventors: Junshan Ruan, Suzhou (CN); Pengfei Du, Suzhou (CN); Limian Wang, Suzhou (CN); Huan Zhou, Suzhou (CN)

(73) Assignee: Suzhou High-Tech Biosciense Co., Ltd., Suzhou (CN)

( * ) Notice: Subject to any disclaimer, the term of this patent is extended or adjusted under 35 U.S.C. 154(b) by 0 days.

(21) Appl. No.: 14/897,488

(22) PCT Filed: Jul. 16, 2014

(86) PCT No.: PCT/CN2014/082290
§ 371 (c)(1),
(2) Date: Dec. 10, 2015

(87) PCT Pub. No.: WO2015/120692
PCT Pub. Date: Aug. 20, 2015

(65) Prior Publication Data
US 2016/0128940 A1    May 12, 2016

(30) Foreign Application Priority Data

Feb. 14, 2014  (CN) .......................... 2014 1 0050783
Jul. 10, 2014  (CN) .......................... 2014 1 0326208

(51) Int. Cl.

| | |
|---|---|
| A61K 9/48 | (2006.01) |
| C08G 63/08 | (2006.01) |
| A61K 9/10 | (2006.01) |
| A61K 9/51 | (2006.01) |
| A61K 47/34 | (2017.01) |
| A61K 9/19 | (2006.01) |
| A61K 31/337 | (2006.01) |
| A61K 9/107 | (2006.01) |
| C08G 63/81 | (2006.01) |
| C08G 63/85 | (2006.01) |
| C08G 63/664 | (2006.01) |
| C08L 67/04 | (2006.01) |
| A61K 9/14 | (2006.01) |

(52) U.S. Cl.
CPC ............... *C08G 63/08* (2013.01); *A61K 9/10* (2013.01); *A61K 9/1075* (2013.01); *A61K 9/19* (2013.01); *A61K 9/5153* (2013.01); *A61K 31/337* (2013.01); *A61K 47/34* (2013.01); *C08G 63/664* (2013.01); *C08G 63/81* (2013.01); *C08G 63/85* (2013.01); *A61K 9/14* (2013.01); *A61K 9/141* (2013.01); *C08L 67/04* (2013.01)

(58) Field of Classification Search
None
See application file for complete search history.

(56) References Cited

U.S. PATENT DOCUMENTS

2004/0247624 A1* 12/2004 Unger ..................... A61K 9/19
424/400

FOREIGN PATENT DOCUMENTS

| CN | 101804021 | 8/2010 |
|---|---|---|
| CN | 101972480 | 2/2011 |
| CN | 102218027 A  * | 10/2011 |
| CN | 102219892 | 10/2011 |
| CN | 102885772 | 1/2013 |

OTHER PUBLICATIONS

Machine translation of CN 10972480.*
Machine translation of CN 102219892.*
Goggle Patents Machine English Translation of CN-102218027-A, Retrieved From Internet Jan. 4, 2018 (Year: 2018).*
International Search Report filed in PCT/CN2014/082290 dated Dec. 2, 2014.

* cited by examiner

*Primary Examiner* — James W Rogers
(74) *Attorney, Agent, or Firm* — Rankin, Hill & Clark LLP (57) ABSTRACT

A docetaxel nano-polymer micelle lyophilized preparation is disclosed including methoxypolyethylene glycol-polylactic acid block copolymer carrier material and docetaxel, the docetaxel being is encapsulated in the carrier material. A mass ratio of the docetaxel to the carrier material is 0.01-0.15. The methoxypolyethylene glycol-polylactic acid block copolymer is formed by ring opening polymerization of D,L-lactide and methoxypolyethylene glycol. A mass ratio of the methoxypolyethylene glycol to the D,L-lactide is 1:0.55-0.65 or 1:0.73-0.89 or 1:0.91-0.99. The mass ratio of the docetaxel to the carrier is further optimized by adjusting a mass ratio of polyester to polyether in the methoxypolyethylene glycol polylactide block copolymer. The encapsulation efficiency of a docetaxel micelle prepared by the block copolymer after being re-dissolved by water can be greater than 90% at 12 hours.

6 Claims, 6 Drawing Sheets

DOCETAXEL NANO-POLYMER MICELLE LYOPHILIZED PREPARATION AND PREPARATION METHOD THEREOF

TECHNICAL FIELD

The present invention belongs to the technical field of drugs, and more particularly, relates to a docetaxel nano-polymer micelle lyophilized preparation and a preparation method thereof.

BACKGROUND

Docetaxel (docetaxel, DTX) is a taxol antineoplastic drug with a molecular formula of C43H53NO14 and a molecular weight of 807.88, which may be combined with a free tubulin to promote the tubulin to be assembled into a stable microtubule, and meanwhile suppress the depolymerization of the tubulin, and cause the generation of a microtubule bundle losing normal functions and fixation of the microtubule, thus suppressing cell mitosis and playing an antineoplastic role. Docetaxel is clinically applied to breast cancer, non-small cell lung cancer, pancreatic cancer, soft tissue sarcoma, head and neck cancer, stomach cancer, ovarian cancer and prostatic cancer or the like, and has notable curative effects no matter it is applied alone or in combination.

However, the docetaxel has such defects like poor water solubility, short half life period and high toxicity at the same time, which limit its clinic applications. At present, docetaxel injections commercially available at home and abroad are prepared by dissolving docetaxel in Tween-80, and need to be diluted using a specialized solvent for injection strictly during clinic application. Its operation requirements are strict and its use method is tedious. Moreover, a large amount of Tween contained in the preparation is easy to cause such adverse reactions as hemolysis and allergy or the like, which needs to take such drugs like dexamethasone in advance for control, is inconvenient for clinic medication, and has low medication safety. So far, this problem has not been preferably solved yet.

A nano-polymer micelle is a drug carrier system developed in recent years direct to indissolvable drugs, which has a core-shell structure, wherein the core is a hydrophobic part, and the shell is a hydrophilic part. The polymer micelle may encapsulate the indissolvable drugs into the core part to solubilize the indissolvable drugs. Compared with a normal solubilizer and latent solvent, the polymer micelle drug carrier system has higher security since it selects biodegradable material as raw materials. Therefore, it has a better application prospect while being served as an encapsulating-carrying accessory for the indissolvable drugs. In multiple technologies, a micelle prepared by the methoxypolyethylene glycol-polylactic acid block copolymer block polymer and the docetaxel is applied to try to solve the difficulty; for example, CN201110105540 discloses a micelle prepared by a methoxypolyethylene glycol-polylactic acid block copolymer and docetaxel, which solves the solubilization problem of docetaxel.

However, the present micelle prepared by the methoxypolyethylene glycol-polylactic acid block copolymer and the docetaxel has poorer stability after being dispersed by water, and the drugs are leaked in a very short time, so that it cannot be further popularized and truly applied during clinic application since its physical stability is not high. In order to solve the problem, CN201010114289 discloses a technology which improves the stability of a micelle after re-dissolving through a method of adding amino acid in a polymer micelle, but the added substances have higher requirements on industrialized production, and a stabilizer added increases the technical complexity of the preparation, and meanwhile, the added amino acid plays a role of degrading the main drugs, which is not suitable for large-scale production.

SUMMARY

Object of the invention: in order to solve the technical problems existed in the prior art, the present invention provides a docetaxel nano-polymer micelle lyophilized preparation, wherein the encapsulation efficiency of the docetaxel nano-polymer micelle after being re-dissolved by water can be greater than 90% at 12 hours (h).

Another technical problem to be solved by the present invention is to provide a preparation method of the foregoing docetaxel nano-polymer micelle lyophilized preparation and applications thereof.

Technical content: to fulfill the foregoing technical object, the present invention adopts the following technical solution.

A docetaxel nano-polymer micelle lyophilized preparation includes methoxypolyethylene glycol-polylactic acid block copolymer carrier material and docetaxel, and the docetaxel is encapsulated in the carrier material, wherein a mass ratio of the docetaxel to the carrier material is 0.01-0.15; the methoxypolyethylene glycol-polylactic acid block copolymer is a block copolymer formed by ring opening polymerization of D,L-lactide and methoxypolyethylene glycol, and a mass ratio of the methoxypolyethylene glycol to the D,L-lactide is 1:0.55-0.65 or 1:0.73-0.89 or 1:0.91-0.99. The mass ratio of the methoxypolyethylene glycol to the D,L-lactide has a great influence on the encapsulation efficiency of the micelle formed by the synthesized block copolymer and re-dissolved by water; therefore, the dosage of the methoxypolyethylene glycol and the D,L-lactide needs to be controlled strictly.

Preferably, a mass ratio of the docetaxel to the carrier material is 0.02-0.09.

The molecular weight of the methoxypolyethylene glycol is 1000-20000, and preferably, the molecular weight of the methoxypolyethylene glycol is 2000 or 5000.

The present invention also provides a preparation method of the foregoing docetaxel nano-polymer micelle lyophilized preparation, including the following steps of:

(1) synthesizing a methoxypolyethylene glycol-polylactic acid block copolymer carrier material;

(2) preparing a drug-carrying micelle aqueous solution using a filming-rehydration method: dissolving docetaxel with a formula ratio and the methoxypolyethylene glycol-polylactic acid block copolymer carrier material prepared in step (1) in an organic solvent, mixing and shaking evenly, performing rotary evaporation to remove the organic solvent, obtaining a gel-like drug film of the drug and the carrier material, then adding water in the drug film to dissolve and disperse the drug film, thus preparing a micelle solution; and wherein the organic solvent is any one or more of acetonitrile, methanol, acetone, methylene chloride, dimethylformamide, dimethyl sulfoxide, tetrahydrofuran, acetone, short chain fatty alcohol and ethyl acetate, 0.5-2 ml of the organic solvent is added per 1 g of the methoxypolyethylene glycol polylactic acid block copolymer carrier material, and preferably, the organic solvent is any one of methylene chloride, methanol, acetone or ethyl acetate; and (3) subjecting the micelle solution prepared in step (2) to filtration sterilization and lyophilizing, thus obtaining the docetaxel nano-polymer micelle lyophilized preparation.

To be specific, the methoxypolyethylene glycol-polylactic acid block copolymer carrier material is prepared through a method as follows: weighing D,L-lactide and methoxypolyethylene glycol with a formula ratio for standby application, subjecting methoxypolyethylene glycol with a formula ratio to vacuum drying for 2-8 h under 60-130° C. in a reactor, performing nitrogen displacement, then adding the D,L-lactide with a formula ratio, adding catalyst stannous octoate, the mass of the stannous octoate occupying 0.05 wt %-0.5 wt % of the total mass of the D,L-lactide and the methoxypolyethylene glycol, then performing evacuation, maintaining a reaction temperature at 60-130° C., performing nitrogen displacement for three times after the D,L-lactide is completely fused, then performing evacuation, ensuring that the reactor has a negative pressure and is sealed or protected by nitrogen, then raising temperature 125-150° C., reacting for 6-20 h, thus obtaining a pale yellow clear viscous liquid after the reaction is completed; adding an organic solvent in the pale yellow clear viscous liquid for dissolution, stirring for 30-50 minutes (min), then continuously adding anhydrous ice diethyl ether and stirring for 20-40 min, standing for 12-24 h at 0-5° C., then performing vacuum drying after suction filtration, thus obtaining the methoxypolyethylene glycol-polylactic acid block copolymer. Wherein, the organic solvent is any one or more of acetonitrile, methanol, acetone, methylene chloride, dimethylformamide, dimethyl sulfoxide, tetrahydrofuran, acetone, short chain fatty alcohol and ethyl acetate, and 0.2-1 ml of the organic solvent is added per 1 g of the pale yellow clear viscous liquid, and preferably, the organic solvent is any one of acetonitrile, methanol, acetone or ethyl acetate. Wherein, the dosage of the anhydrous ice diethyl ether is that 5-10 ml of anhydrous ice diethyl ether is added in 1 g of the pale yellow clear viscous liquid.

Preferably, the dosage of water added in the drug film is 2-40 ml of water per 1 g of the methoxypolyethylene glycol polylactic acid block copolymer carrier material, and more preferably, 5-25 ml of water is added per 1 g of the methoxypolyethylene glycol polylactic acid block copolymer carrier material.

Preferably, in step (2), the conditions for removing the organic solvent via rotary evaporation are that: a rotation velocity is 10-150 rotations per minute (rpm), a temperature is 20-80° C., and a time is 1-4 h.

Advantageous effects: according to the present invention, the block copolymer prepared by methoxypolyethylene glycol and D,L-lactide with a proper mass ratio is employed as the carrier material and meanwhile a proper proportion between the drug and the carrier material is selected, such that the encapsulation efficiency of the docetaxel nano-polymer micelle lyophilized preparation prepared after being re-dissolved by water can be greater than 90% at 12 h, the effect of which is far better than that of a common lyophilized preparation, and complies with the actual situations of clinic drug application, thus satisfying clinic requirements. Through preferred molecular weight and drug-carrying amount of the micelle, the docetaxel is preferably encapsulated by the carrier, thus improving the stability.

DETAILED DESCRIPTION

The foregoing contents of the invention will be further explained in details by means of experimental examples hereinafter, but it should not be understood that the scope of the foregoing subject of the invention is only limited to the following examples, and any technology implemented based on the foregoing contents of the invention shall all fall within the scope of the invention.

Embodiment 1: Preparation of Methoxypolyethylene Glycol-Polylactic Acid Block Copolymer (1) 51.07 g of D,L-lactide and 50.57 g of methoxypolyethylene glycol 2000 were weighed for standby application, the methoxypolyethylene glycol 2000 was subjected to vacuum drying for 7 h under 100□, nitrogen displacement was performed, D,L-lactide was added, and 0.2 g of catalyst stannous octoate was added, evacuation was performed to a vacuum degree of 0.096 Mpa, a reaction temperature was maintained at 100° C., nitrogen displacement was performed for three times after the D,L-lactide was completely fused, evacuation was performed, the reactor was ensured to have a negative pressure and was sealed, then the temperature was raised to 140° C., and reaction was performed for 12 h, thus obtaining a pale yellow clear viscous liquid after the reaction was completed.

Figure 1:
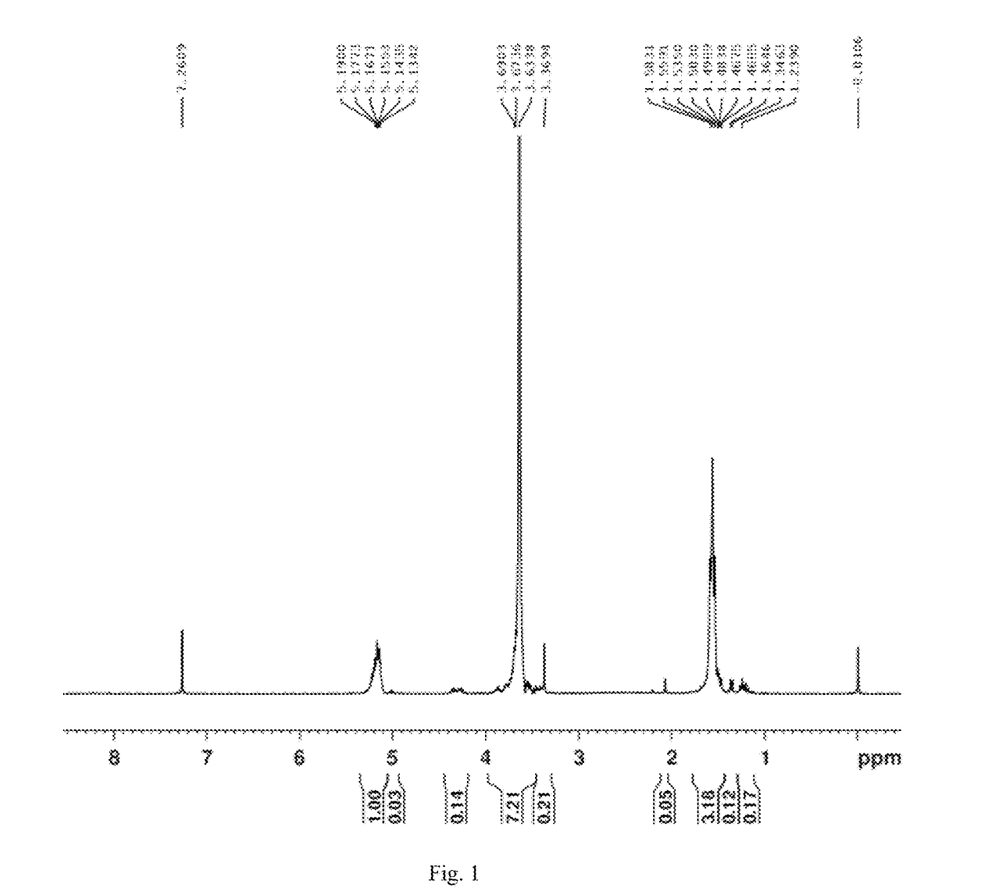
FIG. 1 is a CDCl$_3$ $^1$HNMR profile of a methoxypolyethylene glycol polylactic acid block copolymer.
Figure 2:
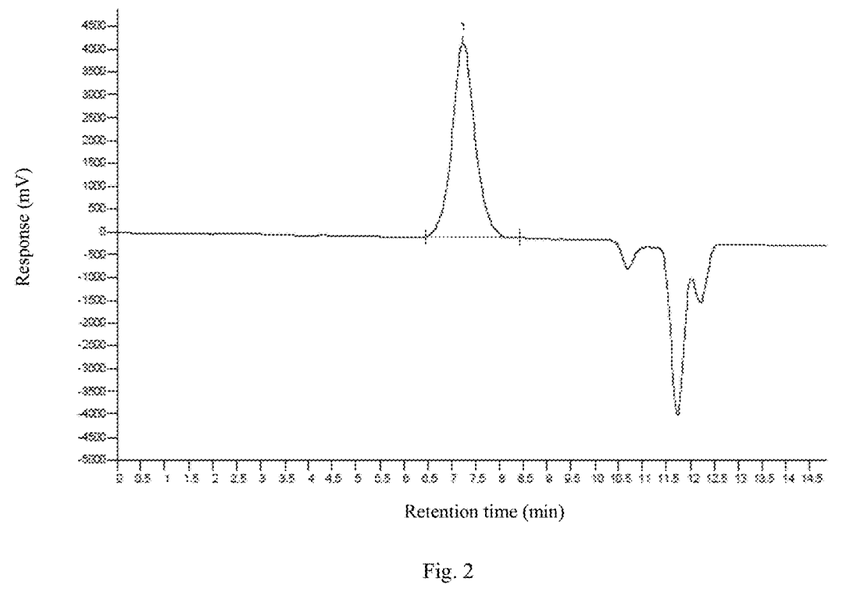
FIG. 2 is a GPC profile of the methoxypolyethylene glycol polylactic acid block copolymer.

(2) 25 ml of methylene chloride was added into the pale yellow clear viscous liquid obtained in step (1), and stirred for 30 min; then 510 ml of anhydrous ice diethyl ether was added, and stirred for 30 min; then standing was performed for 12 h under 0° C., vacuum drying was performed after suction filtration, thus obtaining the methoxypolyethylene glycol-polylactic acid block copolymer; refining was performed for three times according to the foregoing operation process to obtain the methoxypolyethylene glycol-polylactic acid block copolymer, wherein the total yield was about 75%. The obtained polymer was characterized using nuclear magnetic resonance and gel chromatography, wherein the results were as shown in FIG. 1 and FIG. 2. FIG. 1 is characterization of various hydrogens in the methoxypolyethylene glycol-polylactic acid block copolymer, proving that the methoxypolyethylene glycol-polylactic acid block copolymer is synthesized. The detection results of FIG. 2 are as follows: Mp: 6330; Mn: 5887; Mw: 6374; Mz: 6873; M$_{z+1}$: 7393; Mv: 6301; and PDI: 1.08272.

Embodiment 2: Preparation of Methoxypolyethylene Glycol-Polylactic Acid Block Copolymer (1) 48.77 g of D,L-lactide and 51.27 g of methoxypolyethylene glycol 2000 were weighed for standby application, the methoxypolyethylene glycol 2000 was subjected to vacuum drying for 5 h under 120° C., nitrogen displacement was performed, D,L-lactide was added, and then 0.048 g of catalyst stannous octoate was added, evacuation was performed to a vacuum degree of 0.095 Mpa, a reaction temperature was maintained at 120° C., nitrogen displacement was performed for three times after the D,L-lactide was completely fused, evacuation was performed, the reactor was ensured to have a negative pressure and protected by nitrogen, then the temperature was raised to 140° C., and reaction was performed for 14 h, thus obtaining a pale yellow clear liquid after the reaction was completed.

(2) 29 ml of methylene chloride was added into the foregoing pale yellow clear liquid for dissolution, and was stirred and dissolved; then 586 ml of anhydrous ice ethyl ether was added, and stirred for 30 min; standing was performed for 12 h under 5° C., then vacuum drying was performed after suction filtration. Refining was performed for three times according to the foregoing operation process to obtain the methoxypolyethylene glycol-polylactic acid block copolymer, wherein the total yield was about 85%.

Embodiment 3: Preparation of Methoxypolyethylene Glycol-Polylactic Acid Block Copolymer (1) 47.53 g of D,L-lactide and 52.17 g of methoxypolyethylene glycol 2000 were weighed for standby application, the methoxypolyethylene glycol 2000 was subjected to vacuum drying for 7 h under 130° C., nitrogen displacement was performed, 0.3 g of catalyst stannous octoate was added and then D,L-lactide was added, evacuation was performed to a vacuum degree of 0.093 Mpa, a reaction temperature was maintained at 130° C., nitrogen displacement was performed for three times after the D,L-lactide was completely fused, evacuation was performed, the reactor was ensured to have a negative pressure and was sealed, then the temperature was raised to 150° C., and reaction was performed for 6 h, thus obtaining a pale yellow clear liquid after the reaction was completed.

(2) 45 ml of methylene chloride was added into the foregoing pale yellow clear liquid in step (1), and was stirred and dissolved; then 550 ml of anhydrous ice ethyl ether was added, and stirred for 30 min; standing was performed for 12 h under 0° C., then vacuum drying was performed after suction filtration. Refining was performed for three times according to the foregoing operation process to obtain the methoxypolyethylene glycol-polylactic acid block copolymer, wherein the total yield was about 80%.

Embodiment 4: Preparation of Methoxypolyethylene Glycol-Polylactic Acid Block Copolymer (1) 47.11 g of D,L-lactide and 52.85 g of methoxypolyethylene glycol 2000 were weighed for standby application, the methoxypolyethylene glycol 2000 was subjected to vacuum drying for 4 h under 120□, D,L-lactide was added, and then 0.4 g of catalyst stannous octoate was added, evacuation was performed to a vacuum degree of 0.093 Mpa, a reaction temperature was maintained at 120° C., after the D,L-lactide was completely fused, evacuation was performed, the reactor was ensured to have a negative pressure and was sealed, then the temperature was raised to 130° C., and reaction was performed for 18 h, thus obtaining a pale yellow clear viscous liquid after the reaction was completed.

(2) 40 ml of methylene chloride was added into the foregoing pale yellow clear viscous liquid obtained in step (1) for dissolution, and was stirred for 30 min; then 500 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 5: Preparation of Methoxypolyethylene Glycol-Polylactic Acid Bock Copolymer (1) 45.91 g of D,L-lactide and 54.06 g of methoxypolyethylene glycol 2000 were weighed for standby application, the methoxypolyethylene glycol 2000 was subjected to vacuum drying for 3 h under 120° C., nitrogen displacement was performed, then D,L-lactide was added, and 0.25 g of catalyst stannous octoate was added, evacuation was performed, a reaction temperature was maintained at 120° C., after the D,L-lactide was completely fused, nitrogen displacement was performed for three times, the reactor was ensured to have a negative pressure and was sealed, then the temperature was raised to 140° C., and reaction was performed for 12 h, thus obtaining a pale yellow clear viscous liquid after the reaction was completed.

(2) 50 ml of methylene chloride was added into the pale yellow clear viscous liquid obtained in step (1), and stirred for 30 min; then 500 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 75%.

Embodiment 6: Preparation of Methoxypolyethylene Glycol-Polylactic Acid Block Copolymer (1) 44.45 g of D,L-lactide and 55.68 g of methoxypolyethylene glycol 2000 were weighed for standby application, the methoxypolyethylene glycol 2000 was subjected to vacuum drying for 5 h under 110° C., nitrogen displacement was performed, then D,L-lactide was added, and 0.36 g of catalyst stannous octoate was added, evacuation was performed to a vacuum degree of 0.09 Mpa, a reaction temperature was maintained at 110° C., after the D,L-lactide was completely fused, evacuation was performed, the reactor was ensured to have a negative pressure and was sealed, the temperature was controlled to be raised to 140° C., and reaction was performed for 14 h, thus obtaining a pale yellow clear viscous liquid after the reaction was completed.

(2) 60 ml of methylene chloride was added into the pale yellow clear viscous liquid obtained in step (1), and stirred for 30 min; then 660 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 7: Preparation of Methoxypolyethylene Glycol-Polylactic Acid Block Copolymer (1) 39.51 g of D,L-lactide and 61.77 g of methoxypolyethylene glycol 2000 were weighed for standby application, the methoxypolyethylene glycol 2000 was subjected to vacuum drying for 6 h under 100° C., nitrogen displacement was performed, then D,L-lactide was added, and 0.08 g of catalyst stannous octoate was added, evacuation was performed to a vacuum degree of 0.098 Mpa, a reaction temperature was maintained at 100° C., after the D,L-lactide was completely fused, evacuation was performed, the reactor was ensured to have a negative pressure and was sealed, the temperature was controlled to be raised to 140° C., and reaction was performed for 12 h, thus obtaining a pale yellow clear viscous liquid after the reaction was completed.

(2) 50 ml of methylene chloride was added into the pale yellow clear viscous liquid obtained in step (1), and stirred for 30 min; then 540 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 70%.

Embodiment 8: Preparation of Methoxypolyethylene Glycol-Polylactic Acid Block Copolymer (1) 42.17 g of D,L-lactide and 57.89 g of methoxypolyethylene glycol 2000 were weighed for standby application, the methoxypolyethylene glycol 2000 was subjected to vacuum drying for 8 h under 100° C., nitrogen displacement was performed, D,L-lactide was added, and then 0.45 g of catalyst stannous octoate was added, evacuation was performed to a vacuum degree of 0.095 Mpa, a reaction temperature was maintained at 100° C., after the D,L-lactide was completely fused, evacuation was performed, the reactor was ensured to have a negative pressure and was sealed, the temperature was controlled to be raised to 130° C., and reaction was performed for 10 h, thus obtaining a pale yellow clear viscous liquid after the reaction was completed.

(2) 75 ml of methylene chloride was added into the pale yellow clear viscous liquid obtained in step (1) for dissolution, and stirred for 30 min; then 720 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 9: Preparation of Methoxypolyethylene Glycol-Polylactic Acid Block Copolymer (1) 37.53 g of D,L-lactide and 62.71 g of methoxypolyethylene glycol 2000 were weighed for standby application, the methoxypolyethylene glycol 2000 was subjected to vacuum drying for 6 h under 110° C., nitrogen displacement was performed, then D,L-lactide was added, and 0.1 g of catalyst stannous octoate was added, evacuation was performed to a vacuum degree of 0.085 Mpa, a reaction temperature was maintained at 110° C., after the D,L-lactide was completely fused, evacuation was performed, the reactor was ensured to have a negative pressure and was sealed, the temperature was controlled to be raised to 140° C., and reaction was performed for 6 h, thus obtaining a pale yellow clear viscous liquid after the reaction was completed.

(2) 40 ml of methylene chloride was added into the pale yellow clear viscous liquid obtained in step (1), and stirred for 30 min; then 556 ml of anhydrous ice diethyl ether was added, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 80%.

Embodiment 10: Preparation of Methoxypolyethylene Glycol-Polylactic Acid Block Copolymer (1) 35.54 g of D,L-lactide and 64.68 g of methoxypolyethylene glycol 2000 were weighed for standby application, the methoxypolyethylene glycol 2000 was subjected to vacuum drying for 7 h under 100° C., nitrogen displacement was performed, D,L-lactide was added, and then 0.08 g of catalyst stannous octoate was added, evacuation was performed to a vacuum degree of 0.098 Mpa, nitrogen displacement was performed, and a reaction temperature was maintained at 100° C., after the D,L-lactide was completely fused, evacuation was performed, and nitrogen protection is performed, the temperature was controlled to be raised to 140° C., and reaction was performed for 12 h, thus obtaining a pale yellow clear viscous liquid after the reaction was completed.

(2) 35 ml of methylene chloride was added into the pale yellow clear viscous liquid obtained in step (1) for dissolution, and stirred for 30 min; then anhydrous ice diethyl ether was added according to a ratio of 5 to 1 between the volume of the anhydrous ice diethyl ether and the weight of the pale yellow clear viscous liquid (i.e., ml/g) for extraction, and stirred for 30 min; standing was performed for 12 h under 0° C., vacuum drying was performed after suction filtration, and refining was performed for three times according to the foregoing operation process to obtain the methoxypolyethylene glycol-polylactic acid block copolymer, wherein the total yield was about 85%.

Embodiment 11: Preparation of Docetaxel Nano-Polymer Micelle Lyophilized Preparation (1) 20 g of docetaxel, 400 g (mPEG2000:PLA=1:0.99) of methoxypolyethylene glycol-polylactic acid block copolymer prepared in embodiment 1, 4000 ml of water, and 400 ml of organic solvent acetonitrile were taken for standby application.

(2) 1000 ml of acetonitrile was added into standby docetaxel for ultrasound dissolution; then 400 g of methoxypolyethylene glycol-polylactic acid block copolymer was added for continuous dissolution, and then aseptic filtration was performed; then rotary evaporation was performed for 2 h under 50° C. and a rotation velocity of 80 r/min to boil off acetonitrile and obtain a docetaxel polymer gel film, 4000 g of 50° C. water was added quickly for vortex hydration, the temperature of the micelle solution was quickly reduced to 5° C. after complete hydration to obtain the micelle solution, then the micelle solution was subjected to aseptic filtration, sub-packaged and lyophilized.

Embodiments 12-40: Preparation of Docetaxel Nano-Polymer Micelle Lyophilized Preparation The docetaxel nano-polymer micelle lyophilized preparation was prepared with reference to the preparation method in embodiment 11 and according to the dosage in Table 1, wherein a rotation velocity was controlled between 10 and 150 rpm, a temperature was between 20 and 28° C., and the time was 1-4 h.

TABLE 1

| Item | $mPEG_{2000}/$ PLA | $mPEG_{2000}$-PLA (g) | DTX (g) | Organic solvent | Dosage of organic solvent (ml) | Water dosage (ml) |
| --- | --- | --- | --- | --- | --- | --- |
| Embodiment 11 | 1:0.99 | 400 | 4 | Acetonitrile | 400 | 4000 |
| Embodiment 12 | | 400 | 36 | | 600 | 5000 |
| Embodiment 13 | | 400 | 60 | | 800 | 6000 |
| Embodiment 14 | 1:0.95 | 400 | 8 | Acetone | 400 | 4000 |
| Embodiment 15 | | 400 | 30 | | 600 | 5000 |
| Embodiment 16 | | 400 | 40 | | 800 | 6000 |
| Embodiment 17 | 1:0.91 | 400 | 6 | Ethyl acetate | 400 | 4000 |
| Embodiment 18 | | 400 | 40 | | 600 | 5000 |
| Embodiment 19 | | 400 | 50 | | 800 | 6000 |
| Embodiment 20 | 1:0.89 | 400 | 4 | Methylene chloride | 400 | 4000 |
| Embodiment 21 | | 400 | 12 | | 600 | 5000 |
| Embodiment 22 | | 400 | 36 | | 800 | 6000 |
| Embodiment 23 | 1:0.85 | 400 | 8 | Dimethyl-formamide | 400 | 4000 |
| Embodiment 24 | | 400 | 36 | | 600 | 5000 |
| Embodiment 25 | | 400 | 40 | | 800 | 6000 |
| Embodiment 26 | 1:0.80 | 400 | 6 | Dimethyl sulfoxide | 400 | 4000 |
| Embodiment 27 | | 400 | 40 | | 600 | 5000 |
| Embodiment 28 | | 400 | 50 | | 800 | 6000 |
| Embodiment 29 | 1:0.73 | 400 | 8 | Tetrahydro-furan | 400 | 4000 |
| Embodiment 30 | | 400 | 45 | | 600 | 5000 |
| Embodiment 31 | | 400 | 55 | | 800 | 6000 |
| Embodiment 32 | 1:0.65 | 400 | 6 | Methanol | 400 | 4000 |
| Embodiment 33 | | 400 | 36 | | 600 | 5000 |
| Embodiment 34 | | 400 | 60 | | 800 | 6000 |
| Embodiment 35 | 1:0.60 | 400 | 8 | Short chain fatty alcohol | 400 | 4000 |
| Embodiment 36 | | 400 | 40 | | 600 | 5000 |
| Embodiment 37 | | 400 | 55 | | 800 | 6000 |
| Embodiment 38 | 1:0.55 | 400 | 4 | Short chain fatty alcohol | 400 | 4000 |
| Embodiment 39 | | 400 | 36 | | 600 | 5000 |
| Embodiment 40 | | 400 | 40 | | 800 | 6000 |

Figure 3:
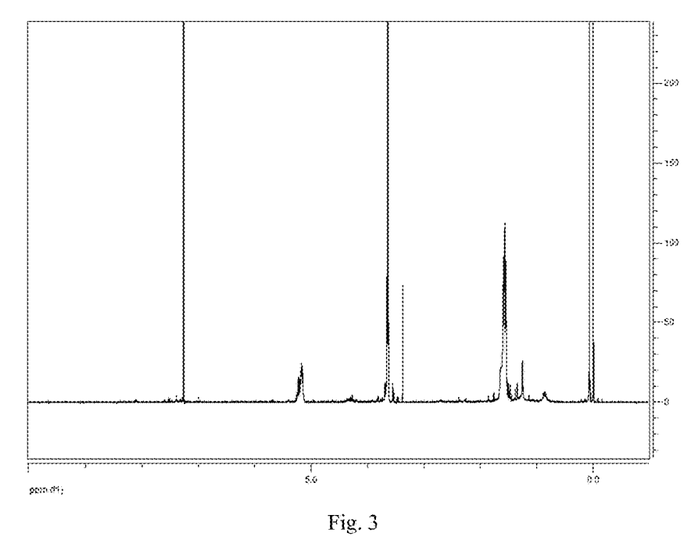
FIG. 3 is a CDCl$_3$ $^1$HNMR profile of a docetaxel polymer micelle lyophilized preparation.
Figure 4:
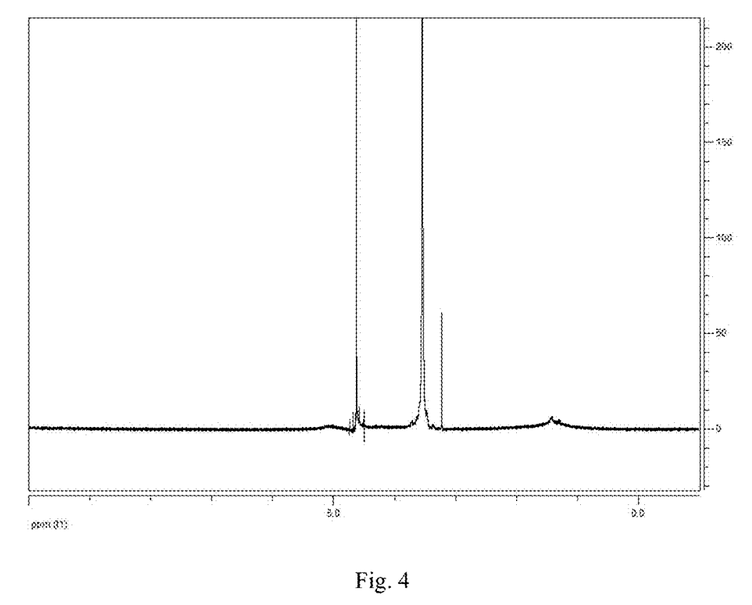
FIG. 4 is a D$_2$O $^1$HNMR profile of the docetaxel polymer micelle lyophilized preparation.
Figure 5:
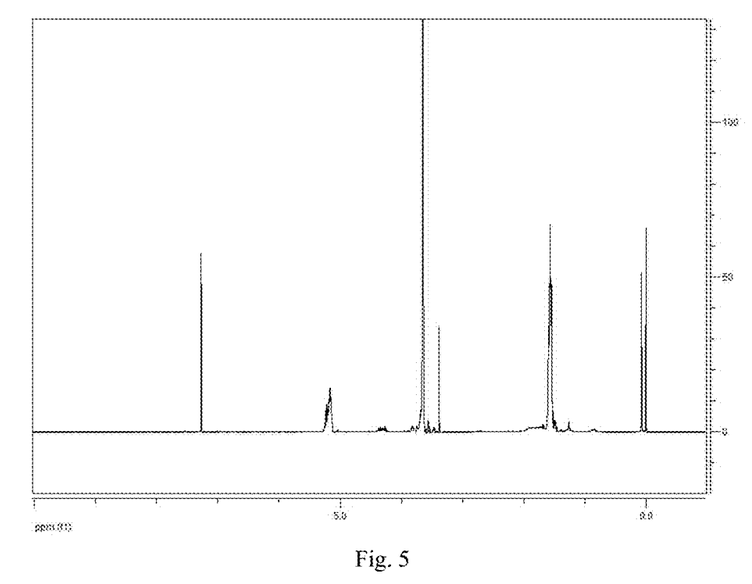
FIG. 5 is a CDCl$_3$ $^1$HNMR profile of the methoxypolyethylene glycol polylactic acid block copolymer.

Embodiments 41: Characterization of Docetaxel Nano-Polymer Micelle Lyophilized Preparation (1) FIG. 3 is a CDCl$_3$ $^1$HNMRprofile of the docetaxel nano-polymer micelle lyophilized preparation prepared in embodiment 11, FIG. 4 is a D$_2$O $^1$HNMR profile of the docetaxel polymer micelle lyophilized preparation prepared in embodiment 11, and FIG. 5 is a CDCl$_3$ $^1$HNMR profile of the methoxypolyethylene glycol polylactic acid block copolymer prepared in embodiment 1. Results show that the docetaxel was encapsulated in the core of the micelle, and a characteristic absorption peak of the docetaxel in the $^1$HNMR profile of the micelle was not found.

Figure 6:
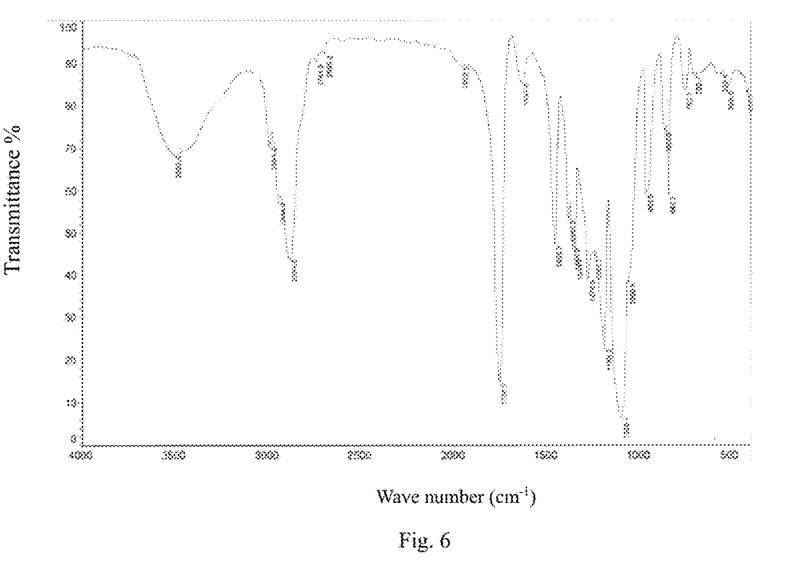
FIG. 6 is an infrared spectrum of the methoxypolyethylene glycol polylactic acid block copolymer.
Figure 7:
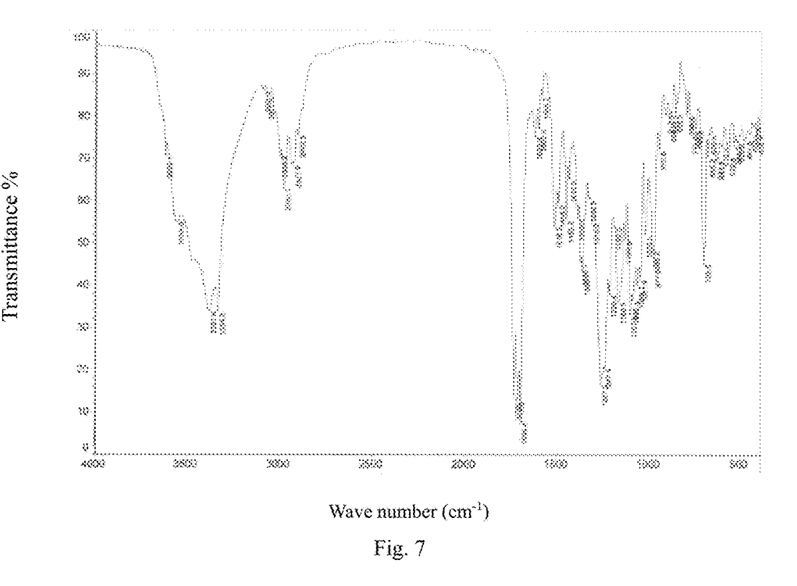
FIG. 7 is an infrared spectrum of docetaxel.
Figure 8:
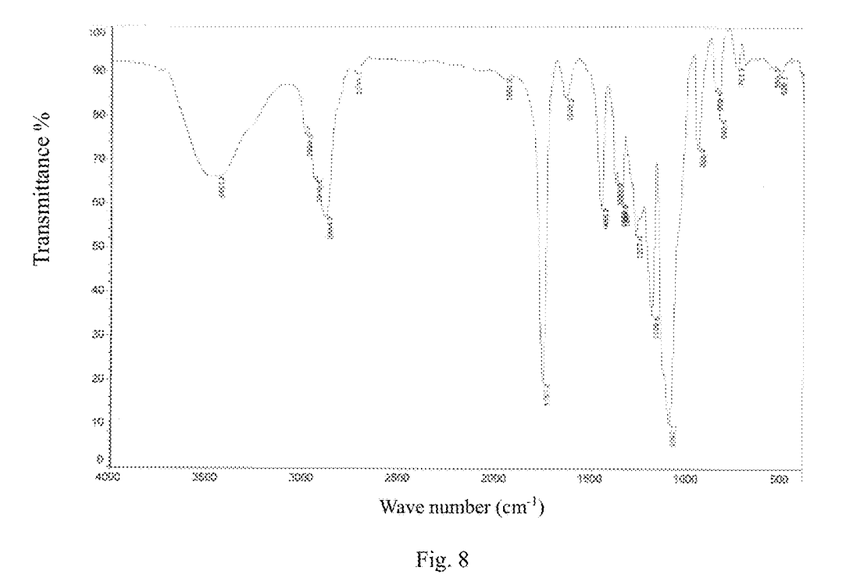
FIG. 8 is an infrared profile of a docetaxel polymer micelle.

(2) A small quantity of the docetaxel nano-polymer micelle lyophilized preparation prepared in embodiment 11, docetaxel and the methoxypolyethylene glycol polylactic acid prepared in embodiment 1 were taken to perform Fourier transform infrared spectrum scanning, wherein results as shown in FIG. 6, FIG. 7 and FIG. 8 proved that the docetaxel was encapsulated in the core of the micelle, and a characteristic absorption peak of the docetaxel in the profile of the micelle was not found.

Figure 9:
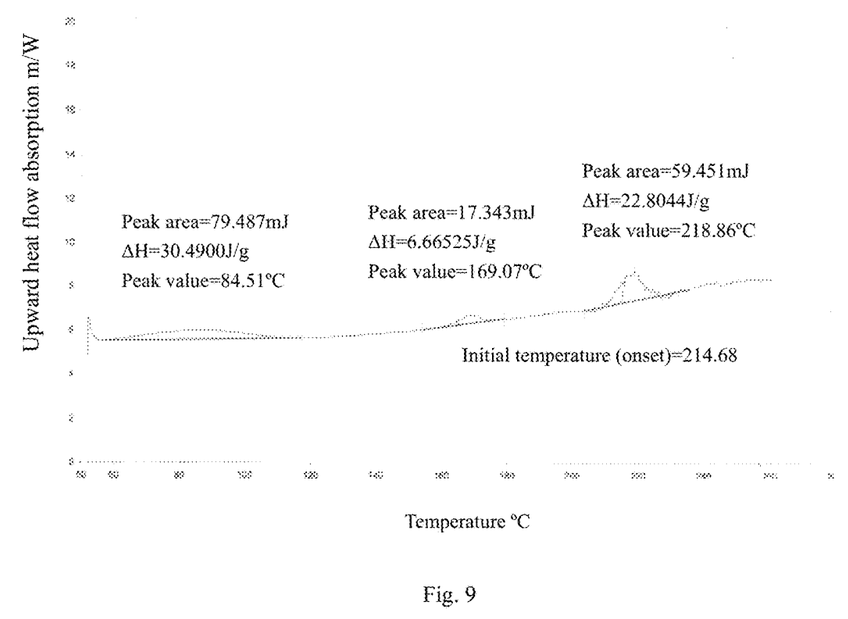
FIG. 9 is a thermal-scanning profile of docetaxel.
Figure 10:
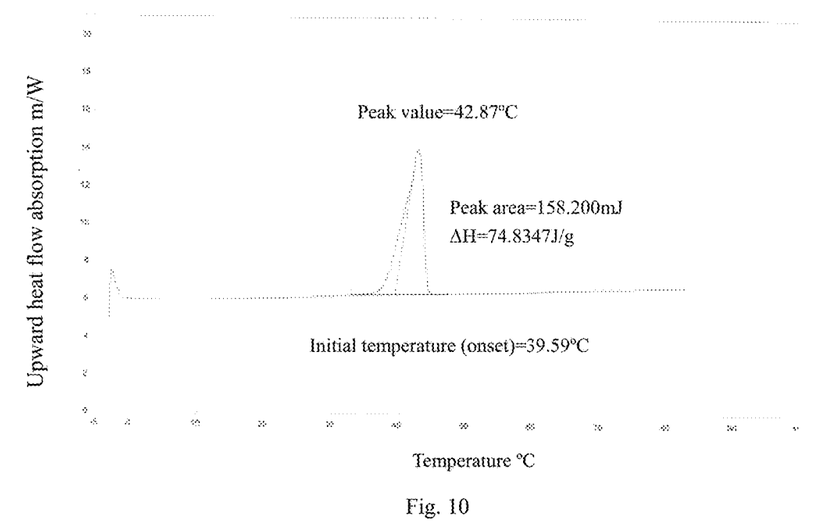
FIG. 10 is a thermal-scanning profile of the methoxypolyethylene glycol polylactic acid block copolymer.
Figure 11:
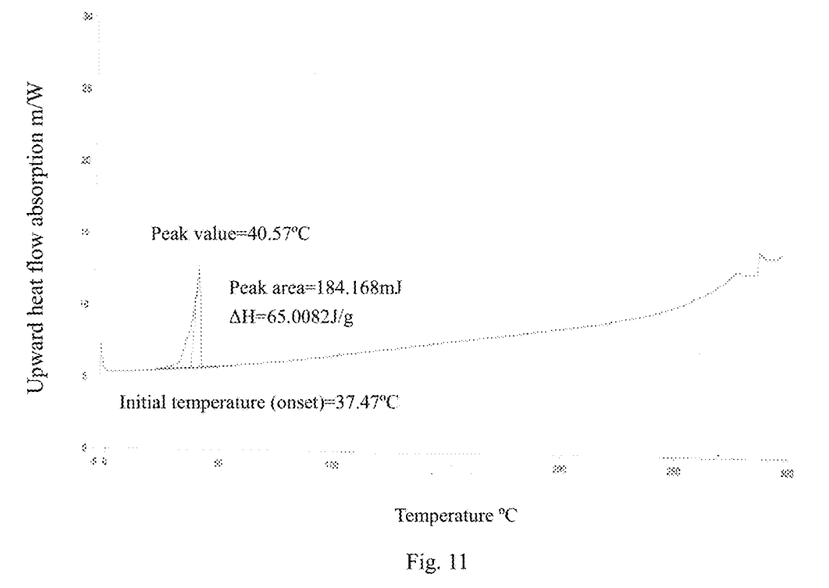
FIG. 11 is a thermal-scanning profile of the docetaxel polymer micelle.

(3) A small quantity of the docetaxel nano-polymer micelle lyophilized preparation prepared in embodiment 11, docetaxel and the methoxypolyethylene glycol polylactic acid prepared in embodiment 1 were taken to perform thermal analysis scanning, wherein results as shown in FIG. 9, FIG. 10 and FIG. 11 proved that the docetaxel was encapsulated in the core of the micelle, and a characteristic absorption peak of the docetaxel in the thermal-scanning profile of the micelle was not found.

Embodiment 42: Encapsulation Efficiency Detection Results of Docetaxel Nano-Polymer Micelle Lyophilized Preparation in Different Time After Re-Dissolving A control drug was prepared according to a recipe 17 (a ratio of polyethylene glycol to polylactic acid is 1:1.2, and a drug-carrying capacity is 6%) in embodiment 1 disclosed in CN201110105540.2. The docetaxel nano-polymer micelle lyophilized preparation was prepared according to the embodiment 11 of the present invention, which was an experimental group, wherein three parallel experiments were performed for the experimental group, and were marked as embodiment 11-1, embodiment 11-2 and embodiment 11-3. Physiological saline was added into the preparation of the control group and the experimental group respectively for dissolution until the concentration was 1 mg/ml (by docetaxel), and then placed under a room temperature (25±2° C.) to detect the encapsulation efficiency thereof in different time. Results were as shown in Table 2.

The encapsulation efficiency of the micelle was measured using high speed centrifugation (10000 r/min, 10 min), wherein the encapsulation efficiency=(1−free drug/total drug)*100%. When determining the encapsulation efficiency of the docetaxel polymer micelle using HPLC, chromatogram conditions used were as follows: ODS was used as a filling material, 0.043 mol/L ammonium acetate aqueous solution-acetonitrile (45:55) was used as a mobile phase, and a detection wavelength was 230 nm. Theoretical plate number calculated by a docetaxel peak should not be less than 2000.

TABLE 2

Encapsulation efficiency detection results of docetaxel nano-polymer micelle lyophilized preparation in different time after re-dissolving

| Time (Hour) | 0 | 0.5 | 1 | 2 | 5 | 8 | 12 | 15 |
|---|---|---|---|---|---|---|---|---|
| Control group | 96.7% | 55% | 45.2% | 33.7% | 27.6% | 15.1% | 10.2% | 8.5% |
| Embodiment 11-1 | 98.3% | 98% | 98% | 97.4% | 97.3% | 96.9% | 90.3% | 81.2% |
| Embodiment 11-2 | 97.3% | 97.0% | 96.4% | 96.0% | 95.6% | 93.1% | 90.4% | 78.5% |
| Embodiment 11-3 | 98.1% | 97.5% | 95.6% | 95.1% | 94.4% | 92.8% | 90.1% | 76.8% |

As shown in Table 2, the encapsulation efficiency of the drug in the experimental group was still greater than 90% at 12 h, while burst release occurred to the drug in the control group at 0.5 h.

The invention claimed is:

1. A method of preparing docetaxel nano-polymer micelle lyophilized preparation, the method consisting of:
    (1) synthesizing a methoxypolyethylene glycol-polylactic acid block copolymer carrier material by ring opening polymerization of D,L-lactide and methoxypolyethylene glycol, wherein a mass ratio of the methoxypolyethylene glycol to the D,L-lactide is 1:0.91-0.99;
    (2) preparing a drug-carrying micelle aqueous solution using a filming-rehydration process consisting of: dissolving docetaxel and the methoxypolyethylene glycol-polylactic acid block copolymer carrier material prepared in step (1) in an organic solvent at a mass ratio of the docetaxel to the methoxypolyethylene glycol-polylactic acid block copolymer carrier material of 0.01-0.15, mixing and shaking evenly, performing rotary evaporation to remove the organic solvent, obtaining a gel-like drug film of the docetaxel and the methoxypolyethylene glycol-polylactic acid block copolymer carrier material, then adding water to the drug film to dissolve and disperse the drug film, thus preparing the drug-carrying micelle aqueous solution; and
    (3) subjecting the drug carrying micelle aqueous solution prepared in step (2) to filtration sterilization and lyophilizing, thus obtaining the docetaxel nano-polymer micelle lyophilized preparation;
    wherein when the drug-containing micelles are dispersed in water, the micelles have an encapsulation efficiency of greater than 90% at 12 hours, and
    wherein synthesizing the methoxypolyethylene qlvcol-polylactic acid block copolymer carrier material includes:
        weighing D,L-lactide and methoxypolyethylene glycol, subjecting methoxypolyethylene glycol to vacuum drying for 2-8 hours at 60-130° C. in a reactor, performing nitrogen displacement, then adding the D,L- lactide, adding stannous octoate as a catalyst, the mass of the stannous octoate occupying 0.05 wt %-0.5 wt % of the total mass of the D,L-lactide and the methoxypolyethylene glycol, then performing evacuation, maintaining a reaction temperature at 60-130° C., performing nitrogen displacement for three times, then performing evacuation, ensuring that the reactor has a negative pressure and is sealed or protected by nitrogen, then raising temperature to 125-150° C., reacting for 6-20 hours, thus obtaining a pale yellow clear viscous liquid after the reaction is completed; adding an organic solvent in the pale yellow clear viscous liquid for dissolution, stirring for 30-50 minutes, then continuously adding ice-cold anhydrous diethyl ether and stirring for 20-40 minutes, letting the liquid stand for 12-24 hours at 0-5° C., then performing suction filtration followed by vacuum drying, thus obtaining the methoxypolyethylene glycol-polylactic acid block copolymer carrier material.

2. The method according to claim 1, wherein the organic solvent is selected from the group consisting of acetonitrile, methanol, acetone, methylene chloride, dimethylformamide, dimethyl sulfoxide, tetrahydrofuran, acetone, short chain fatty alcohol, ethyl acetate and mixtures thereof, and 0.2-1 ml of the organic solvent is added per 1 g of the pale yellow clear viscous liquid.

3. The method according to claim 1, wherein 5-10 ml of ice-cold anhydrous diethyl ether is added per 1 g of the pale yellow clear viscous liquid.

4. The method according to claim 1, wherein
   the organic solvent in step (2) is selected from the group consisting of acetonitrile, methanol, acetone, methylene chloride, dimethylformamide, dimethyl sulfoxide, tetrahydrofuran, acetone, short chain fatty alcohol, ethyl acetate and mixtures thereof, and
   0.5-2 ml of the organic solvent is added per 1 g of the methoxypolyethylene glycol polylactic acid block copolymer carrier material.

5. The method according to claim 1, wherein 2-40 ml of water is added per 1 g of the methoxypolyethylene glycol polylactic acid block copolymer carrier material.

6. The method according to claim 1, wherein the conditions for removing the organic solvent via rotary evaporation in step (2) are: a rotation velocity is 10-150 rotations per minute, a temperature is 20-80° C., and a time is 1-4 hours.

* * * * *